United States Patent [19]

Lücke et al.

[11] Patent Number: 5,079,265

[45] Date of Patent: Jan. 7, 1992

[54] COMPOSITION AND METHODS FOR PROVIDING OPTIMUM BIOAVAILABILITY OF THE ACTIVE INGREDIENT 2-HYDROXY-5-METHYLLAUROPHENOXIME (HMLO)

[75] Inventors: Lothar Lücke; Gerhard Fries; Günter Voigt, all of Magdeburg; Reinhard Neubert, Halle; Walter Fürst, Halle-Neustadt; Jürgen Slapke, Schwanebeck; Tankred Schewe, Berlin, all of German Democratic Rep.

[73] Assignee: VEB Fahlberg-List Chemische und pharmazeutische Fabriken, Magdeburg, German Democratic Rep.

[21] Appl. No.: 476,193

[22] Filed: Feb. 7, 1990

[30] Foreign Application Priority Data

Mar. 29, 1989 [DD] German Democratic Rep. ................................ 3269784

[51] Int. Cl.⁵ .............................................. A61K 31/15

[52] U.S. Cl. .................................... 514/640; 514/177; 514/182; 514/946

[58] Field of Search ....................... 514/640, 177, 182

[56] References Cited

U.S. PATENT DOCUMENTS 4,816,487 3/1989 Schewe et al. ...................... 514/640

OTHER PUBLICATIONS

Chemical Abstracts 86:95918t (1977).
Chemical Abstracts 108:226,860r (1988).

*Primary Examiner*—Leonard Schenkman
*Attorney, Agent, or Firm*—Jordan and Hamburg

[57] ABSTRACT

Improved bioavailability, particularly when the drug is administered orally, of the active ingredient 2-hydroxy-5-methyllaurophenoxime (HMLO) of a pharmaceutical preparation is achieved by improving the absorption of the active ingredient HMLO significantly by including bile acids in the preparation. As bile acids, it is possible to use, for example, desoxychloic acid or dehydrocholic acid or a mixture of the two in the form of their salts.

6 Claims, No Drawings

COMPOSITION AND METHODS FOR PROVIDING OPTIMUM BIOAVAILABILITY OF THE ACTIVE INGREDIENT 2-HYDROXY-5-METHYLLAUROPHENOXIME (HMLO)

BACKGROUND OF THE INVENTION

The invention is directed to a method for the production of a drug in a form, which is suitable for oral administration, contains the active ingredient 2-hydroxy-5-methyllaurophenoxime (HMLO) and clearly improves the bioavailability of this active ingredient and thus offers the prerequisites for the optimum treatment of bronchial asthma and of allergic, rheumatic and inflammatory diseases of different origin.

As is well known, there is a relationship between the solubility, the absorption and the bioavailability of a substance. Drugs of very low solubility are frequently also not absorbed very well. In general, it may be expected that problems with respect to the bioavailability will be encountered if the solubility is less than 0.3% (Ritschel, W. A., Angewandte Biopharmazie (Applied Biopharmacy), Wissenschaftliche Verlagsgesellschaft (Scientific Publishing Company) MBH Stuttgart 1953, page 53; Thoma, K. Oesterreich.-Apotheken-Ztg. (Austrian Pharmacy Journal) 32 (1978) 8, page 157).

It is well known that the bioavailability of drugs of low solubility can be varied for example, by a chemical modification of the drug, by changing the molecular size, by creating suitable pH conditions, by selecting a suitable form of administration, by micronizing, by preparing so-called solid dispersions, as well as by using absorption accelerators.

For example, according to W. A. Ritschel (Ritschel, W. A., Angewandte Biopharmazie (Applied Biopharmacy), Wissenschaftliche Verlagsgesellschaft (Scientific Publishing Company) MBH Stuttgart 1973) organic solvents, such as ethanol, fatty alcohols and fatty esters, surface active materials such as nonionic, anionic and cationic surfactants, saponins, enzymes, complexing agents and carbohydrates, such as sorbitol and glucosamine, are used to improve the bioavailability.

The absorption of the drug HMLO, which has a low solubility, has been modified by using solutions and emulsions, which contain, for example, oils, particularly cotton seed oil, peanut oil, cashew nut oil, corn oil, olive oil, castor oil and sesame oil (GDR Patent DD 235 450 A 1). By these means, the bioavailability can be increased. However, such a preparation is unsuitable for a long-term treatment, because not only can such a treatment disadvantageously affect the fat metabolism, but it can also lead to the necessity of terminating the treatment due to the occurrence of diarrhea.

In the same patent, a plurality of additional auxiliary materials is given, which can be used for a formulation, without any proof being presented of the effect on absorption.

SUMMARY OF THE INVENTION

It is an object of the invention to improve the bioavailability of the active ingredient HMLO after oral administration through the use of auxiliaries, which modify the absorption.

It is a further object of the invention to provide auxiliary materials which improve the absorption and thus the bioavailability without negatively affecting the tolerance to the preparation of the person being treated.

Surprisingly it was found that, in comparison to the pure active ingredient as well as to all known pharmaceutical preparations, the absorption of the active ingredient HMLO is improved clearly in vitro and in vivo in the presence of bile acids. This improvement is observed also in comparison with the oily preparation, although the same mechanism for affecting the absorption obviously forms the basis for this preparation.

In the oily preparations, the oil probably does not function as a solubilizer or surfactant; instead, it stimulates the secretion of bile and thus contributes to the improved absorption. If the bile acid is added to the active ingredient, the same or a quantitatively improved effect is achieved, but the unwanted side effects, which are associated with the increased supply of oil, cannot occur.

DETAILED DESCRIPTION OF PREFERRED EMBODIMENTS

As bile acids, desoxycholic acid or dehydrocholic acid or a mixture of the two in the form of their salts, for example, can be used in the molar ratio of bile acid to HMLO of 0.1:1 to 10:1 and preferably of 0.5:1 to 1:0.5.

The active ingredient HMLO can be formulated with the bile acid or the mixture of bile acids in the form of solutions, suspensions, capsules, granulates, tablets or sugar-coated pills; preferably, it is formulated in the form of granulates or tablets.

For this purpose, the HMLO active ingredient is advisably mixed homogeneously with the salt of the bile acid or acids and the usual tableting auxiliaries, such as lactose, potato starch and sugar, and subsequently granulated with a polyvinyl alcohol solution. The granulate obtained is dried, screened and mixed with appropriate lubricants and flow regulators, such as calcium stearate and talc. The granulate obtained can either be administered directly or pressed into tablets.

The invention is illustrated by the following examples without, however, being limited by these.

EXAMPLE 1:

| Composition of the Formulation | |
|---|---|
| 360 g | HMLO (active ingredient) |
| 240 g | sodium desoxycholate |
| 214 g | lactose |
| 100 g | potato starch |
| 10 g | sugar |
| 9 g | gelatin |
| 30 g | calcium stearate |
| 37 g | talc |

HMLO active ingredient (360 g), 240 g of sodium desoxycholate, 214 g of lactose, 100 g of potato starch and 10 g of sugar are mixed dry, for example, in a fluidized bed granulator, and granulated by spraying in 250 mL of an aqueous gelatin solution (9 g of gelatin), which has a temperature of about 333° K. The granulate, so obtained, is screened and mixed homogeneously with the external phase, consisting of 30 g of calcium stearate and 37 g of talc. The product obtained can be used directly as the administration form or pressed into tablets weighing 200 mg and containing 100 mg of active ingredient.

EXAMPLE 2

| Composition of the Formulation | |
| --- | --- |
| 500 g | HMLO (active ingredient) |
| 120 g | sodium dehydrocholate |
| 204 g | lactose |
| 90 g | potato starch |
| 20 g | sugar |
| 9 g | gelatin |
| 20 g | calcium stearate |
| 37 g | talc |

HMLO active ingredient (500 g), 120 g of sodium dehydrocholate, 204 g of lactose, 90 g of potato starch and 20 g of sugar are mixed dry, for example, in a fluidized bed granulator, and granulated by spraying in 250 mL of an aqueous solution of gelatin (9 g of gelatin), which has a temperature of about 333° C. The granulate obtained is screened and mixed homogeneously with the external phase, consisting of 20 g of calcium stearate and 37 of talc. The product, so obtained, can be used directly as the administration form or pressed into tablets weighing 400 mg and containing 200 mg of active ingredient.

EXAMPLE 3

Effect of Different Auxiliaries on the Solubility of HMLO Active Ingredient in Water at 293° K.

| Auxiliary | Auxiliary Concentration in % | Solubility (microgram/mL) |
| --- | --- | --- |
| Sodium desoxycholate | 0.75 | 2750.0 |
| Tween (R) 80 | 0.75 | 130.0 |
| Benzalkonium bromide | 1.00 | 24.0 |
| PVA | 10.00 | — |
| Propylene glycol | 1.00 | 2.3 |
| Polyethylene glycol 6500 | 10.00 | 1.0 |
| Heweten 40 | 10.00 | — |

Pure HMLO (active ingredient) is insoluble in water.

EXAMPLE 4

In Vivo Absorption of HMLO Active Ingredient by the Rabbits After Oral Administration as a Function of the Auxiliaries Used.

| Preparation | Dose mg/kg | Number of Animals | MRT (h)$^{24\,h}$ | AUC ($\mu g \times$ h)/mL |
| --- | --- | --- | --- | --- |
| HMLO active ingredient without auxiliaries | 12 | 4 | — | — |
| Oily Preparation | 12 | 6 | 14.7 | 18.7 |
| Desoxycholic acid Preparation | 12 | 6 | 13.6 | 19.4 |

It can be seen that, without auxiliaries, the HMLO active ingredient is not absorbed to a measurable extent. The absorption is clearly affected by the use of oil as auxiliary. This effect, however, is distinctly exceeded by the use of bile acids.

We claim:

1. A pharmaceutical preparation comprising a mixture of 2-hydroxy-5-methyllaurophenoxime as an active ingredient and at least one bile acid as an absorption agent, the molar ratio of bile acids to 2-hydroxy-5-methyllaurophenoxime being from 0.1:1 to 10:1.

2. A pharmaceutical preparation according to claim 1 in which the at least one bile acid is selected from the group consisting of desoxycholic acid, dehydrocholic acid and salts of desoxycholic acid and dehydrocholic acid.

3. A pharmaceutical preparation according to claim 2 in which the molar ratio of bile acids to 2-hydroxy-5-methyllaurophenoxime is from 0.5:1 to 1:0.5.

4. A method of treating a person suffering from bronchial asthma or allergic, rheumatic or other inflammatory diseases comprising orally administering to the person a pharmaceutical preparation according to claim 1.

5. A method of treating a person suffering from bronchial asthma or allergic, rheumatic or other inflammatory diseases comprising orally administering to the person a pharmaceutical preparation according to claim 2.

6. A method of treating a person suffering from bronchial asthma or allergic, rheumatic or other inflammatory diseases comprising orally administering to the person a pharmaceutical preparation according to claim 3.

* * * * *